United States Patent
Andersen et al.

(10) Patent No.: US 9,080,200 B2
(45) Date of Patent: Jul. 14, 2015

(54) METHOD OF QUALITY CONTROL TESTING A FACTOR XIII CONTAINING SAMPLE

(75) Inventors: Mette Dahl Andersen, Værløse (DK); Gunhild K. Kristiansen, Bagsværd (DK); Pernille Charlotte Svane, Søborg (DK); Lene Hørlyck, Birkerød (DK); Mette Schrøder, Valby (DK)

(73) Assignee: Novo Nordisk Healthcare A/G, Zurich (CH)

( * ) Notice: Subject to any disclaimer, the term of this patent is extended or adjusted under 35 U.S.C. 154(b) by 1061 days.

(21) Appl. No.: 13/124,964

(22) PCT Filed: Oct. 23, 2009

(86) PCT No.: PCT/EP2009/063973
§ 371 (c)(1),
(2), (4) Date: Jun. 29, 2011

(87) PCT Pub. No.: WO2010/046468
PCT Pub. Date: Apr. 29, 2010

(65) Prior Publication Data
US 2011/0265557 A1 Nov. 3, 2011

Related U.S. Application Data

(60) Provisional application No. 61/109,520, filed on Oct. 30, 2008.

(30) Foreign Application Priority Data

Oct. 24, 2008 (EP) .................................. 08167476

(51) Int. Cl.
*C12Q 1/56* (2006.01)
*G01N 33/86* (2006.01)

(52) U.S. Cl.
CPC ....... *C12Q 1/56* (2013.01); *G01N 33/86* (2013.01); *G01N 2333/91085* (2013.01)

(58) Field of Classification Search
CPC .......... G01N 2333/00; G01N 2333/90; G01N 2333/91045; G01N 2333/9108; G01N 33/48; G01N 33/96; G01N 33/5002; G01N 2030/00; G01N 2030/02; G01N 2030/022; G01N 2030/027; G01N 2030/96; Y10S 435/973; Y10S 436/80; C12N 9/00; C12N 9/1044; C12N 9/104; C12N 9/1025; C12Q 1/00; C12Q 1/56

See application file for complete search history.

(56) References Cited

U.S. PATENT DOCUMENTS 5,387,503 A * 2/1995 Selmer et al. .................... 435/5
5,508,202 A * 4/1996 Enomoto et al. .............. 436/69
5,612,456 A * 3/1997 Bishop et al. ................ 530/381

FOREIGN PATENT DOCUMENTS

JP       2005516180 A       6/2005
WO     WO 2006/018164     2/2006
WO     WO 2006021584 A2 *  3/2006

OTHER PUBLICATIONS

Tosoh Bioscience. TSKgel DEAE-NPR. Datasheet (and .pdf) [online] Tosoh Bioscience LLC. Oct. 2008. [retrieved on Jun. 19, 2014]. Retrieved from the Internet: <http://www.separations.us.tosohbioscience.com/Products/HPLCColumns/IonExchange/AnionExchange/TSKgelDEAE-NPR/7b4A878658-0846-4AF9-9780-AFEE3672B06D%7d&NRCACHEHINT=Guest>pp. 1-4. specif p. 3.*
Elssner, A. et al. 1999. Inhibition of factor XIIIa-mediated incorporation of fibronectin into fibrin by pulmonary surfactant. American Journal of Physiology 276: L625-L630. specif. L625-L626.*
Credo, R.B. et al. 1978. Ca2+-related regulatory function of fibrinogen. Proceedings of the National Academy of Sciences USA 75(9): 4234-4237. specif. pp. 4234-4236.*
Zettner, A. et al. 1964. Application of atomic absorption spectrophotometry in the determination of calcium in serum. Atomic Absorption Spectrophotometry 10(10): 869-890. specif. pp. 869, 871, 873-874.*
Oertal K. et al., "A highly sensitive fluorometric assay for determination of human coagulation factor XIII in plasma", Journal : Analytical Biochemistry, Year Aug. 15, 2007, vol. 367, No. 2, pp. 152-158.
Muszbek, L. (2007) "Factor XII: recommended terms and abbreviations." Journal of Thrombosis and Haemostasis. vol. 5: 181-183.
Muszbek, L. (1993) "Platelet factor XIII becomes active without the release of activation peptide during platelet activation." Thrombosis and Haemostasis vol. 69: 282-285.
Muszbek, L. (1999) "Blood Coagulation Factor XIII: Structure and Function" Thrombosis Research vol. 94: 271-305.
Polgar et al., Biochemical Journal, 1990, vol. 267, pp. 557-560.
Karges et al., Seminars in Thrombosis and Hemostasis, 1996, vol. 22, No. 5, pp. 427-436.
Muszbek et al., Thrombosis and Haemostasis, 1995, vol. 73, No. 4, pp. 702-705.

* cited by examiner

*Primary Examiner* — John S Brusca
*Assistant Examiner* — Sharon M Papciak
(74) *Attorney, Agent, or Firm* — Leon Y. Lum (57) ABSTRACT

The invention relates to a method of quality control testing a Factor XIII (FXIII) containing sample which comprises the step of detecting the presence of and/or measuring the concentration of pre-activated FXIII (FXIIIao) in said sample and to a quality control kit for determining the quality of a Factor XIII (FXIII) containing sample. Preferably, an anion-exchange chromatographic column is used, as well as the fluorescent substrate Abz-NE (Cad-Dnp) EQVS PLTLLK-OH.

13 Claims, 6 Drawing Sheets

SEQUENCE LISTING

```
<160> NUMBER OF SEQ ID NOS: 1

<210> SEQ ID NO 1
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)

<400> SEQUENCE: 1

Glu Gln Val Ser Pro Leu Thr Leu Leu Lys
1               5                   10
```

METHOD OF QUALITY CONTROL TESTING A FACTOR XIII CONTAINING SAMPLE

CROSS-REFERENCE TO RELATED APPLICATIONS

This application is a 35 U.S.C. §371 national stage application of International Patent Application PCT/EP2009/063973 (published as WO 2010/046468 A1), filed Oct. 23, 2009, which claimed priority of European Patent Application 08167476.4, filed Oct. 24, 2008; and this application further claims priority under 35 U.S.C. §119 of U.S. Provisional Application 61/109,520 filed Oct. 30, 2008.

FIELD OF THE INVENTION

The invention relates to a method of quality control testing a Factor XIII (FXIII) containing sample which comprises the step of detecting the presence of and/or measuring the concentration of pre-activated FXIII (FXIIIa$^O$) in said sample and to a quality control kit for determining the quality of a Factor XIII (FXIII) containing sample.

BACKGROUND OF THE INVENTION

Blood coagulation is a process consisting of a complex interaction of various blood components (or factors) that gives rise to a fibrin clot. Generally, the blood components, which participate in what has been referred to as the coagulation "cascade", are enzymatically inactive proteins (proenzymes or zymogens) that are converted to proteolytic enzymes by the action of an activator (which itself is an activated clotting factor). Coagulation factors that have undergone such a conversion are generally referred to as "active factors", and are designated by the addition of the letter "a" to the name of the coagulation factor (e. g. Factor XIIIa).

FXIII is predominantly found in the zymogen form in either recombinant FXIII (FXIII-A$_2$), plasma FXIII (FXIII-A$_2$B$_2$) or intracellular FXIII (FXIII-A$_2$). In plasma, during blood clotting, the thrombin activation pathway predominates. Thrombin cleaves an activation peptide of 37 amino acid residues from the N-terminal part of each FXIII-A subunit and in presence of Ca$^{2+}$ generates the active form FXIIIa*. Conversely, intracellular FXIII is not accessible to thrombin and it has been observed that non-proteolytic activation occurs under certain conditions to yield an active FXIII species, (FXIIIa$^O$) which contains all 1-731 amino acids in each FXIII-A subunit and thus has not been cleaved by activated thrombin (Polgar et al (1990) Biochem. J. 267, 557-560).

For patients with severe hemophilia, blood coagulation factors, such as FXIII are administered to aid in the blood clotting process. FXIII is to be administrated in its in-active/zymogen form, which first will be naturally activated in vivo on demand, e.g when a laceration occurs. As a quality parameter of the product the content of pre-activated FXIII (FXIIIa$^O$) needs to be measured and kept to a minimum. However, there is a likelihood that certain amounts of FXIII may be non-proteolytically activated to FXIIIa$^O$ within a pharmaceutical formulation which would consequently increase the risk of non-specific coagulation.

There is thus a great need for a method of measuring the quality of a FXIII containing formulation to ensure the safety of FXIII products and to ensure that treatment of hemophilia is optimised.

SUMMARY OF THE INVENTION

According to a first aspect of the invention there is provided a method of quality control testing a Factor XIII (FXIII) containing sample which comprises the step of detecting the presence of and/or measuring the concentration of pre-activated FXIII (FXIIIa$^O$) in said sample.

According to a second aspect of the invention there is provided a quality control kit for determining the quality of a Factor XIII (FXIII) containing sample which comprises pre-activated FXIII (FXIIIa$^O$) detecting and/or measuring components and instructions to use said kit in accordance with the methods as defined herein.

BRIEF DESCRIPTION OF THE FIGURES

FIG. 5 shows anion exchange HPLC chromatograms with zymogen FXIII-A$_2$ (FIG. 5A) and activated FXIIIa$^O$ (FIG. 5B)

DETAILED DESCRIPTION OF THE INVENTION

According to a first aspect of the invention there is provided a method of quality control testing a Factor XIII (FXIII) containing sample which comprises the step of detecting the presence of and/or measuring the concentration of pre-activated FXIII (FXIIIa$^O$) in said sample.

The invention provides a method for measuring FXIII activity in the absence of thrombin, thus both FXIIIa$^O$ and already formed FXIIIa* in a sample will yield signal. This activity is termed FXIIIa since the activation mechanism is not distinguished upon. In reality, FXIIIa* is easily detected by standard HPLC and MS methods since it has a different mass from FXIII. Furthermore, the generation of FXIIIa* is easily avoided in pharmaceutical FXIII preparations. In contrast FXIIIa$^O$ has the identical mass to FXIII and is thus more difficult to detect by standard methods. In the absence of FXIIIa* in samples, the enzymatic assay method determines the levels of FXIIIa$^O$.

The invention provides significant advantages with respect to the accurate and sensitive determination of pre-activated FXIII which has been found to be essential for assessing and ensuring the quality of FXIII containing samples. In particular, it has been found that the methods of the invention are able to detect trace amounts of pre-activated FXIII among zymogen FXIII with a sensitivity of approximately 0.1%. The invention therefore provides an accurate determination of the quality and effectiveness of a given FXIII containing formulation which is directly correlated with the amount of pre-activated FXIII present within the formulation. For example, it could be envisaged that batches of formulations containing FXIII would be discarded if a sample from a formulation contained more than a certain percentage of pre-activated FXIII (e.g. more than 0.3, 0.6, 1 or 2%).

References herein to "pre-activated FXIII" or "FXIIIa$^O$" each refer to FXIII which has been non-proteolytically activated in the absence of thrombin.

References herein to "activated FXIII" refer to FXIII which has been proteolytically activated in the presence of thrombin.

In one embodiment, the presence of FXIIIa$^O$ in said sample is detected by chromatographic separation.

According to a further aspect of the invention there is provided a method of detecting the presence of and/or measuring the concentration of pre-activated FXIII (FXIIIa$^O$) which comprises a chromatographic separation step.

In one embodiment, the chromatographic separation comprises anion exchange HPLC.

Figure 5:
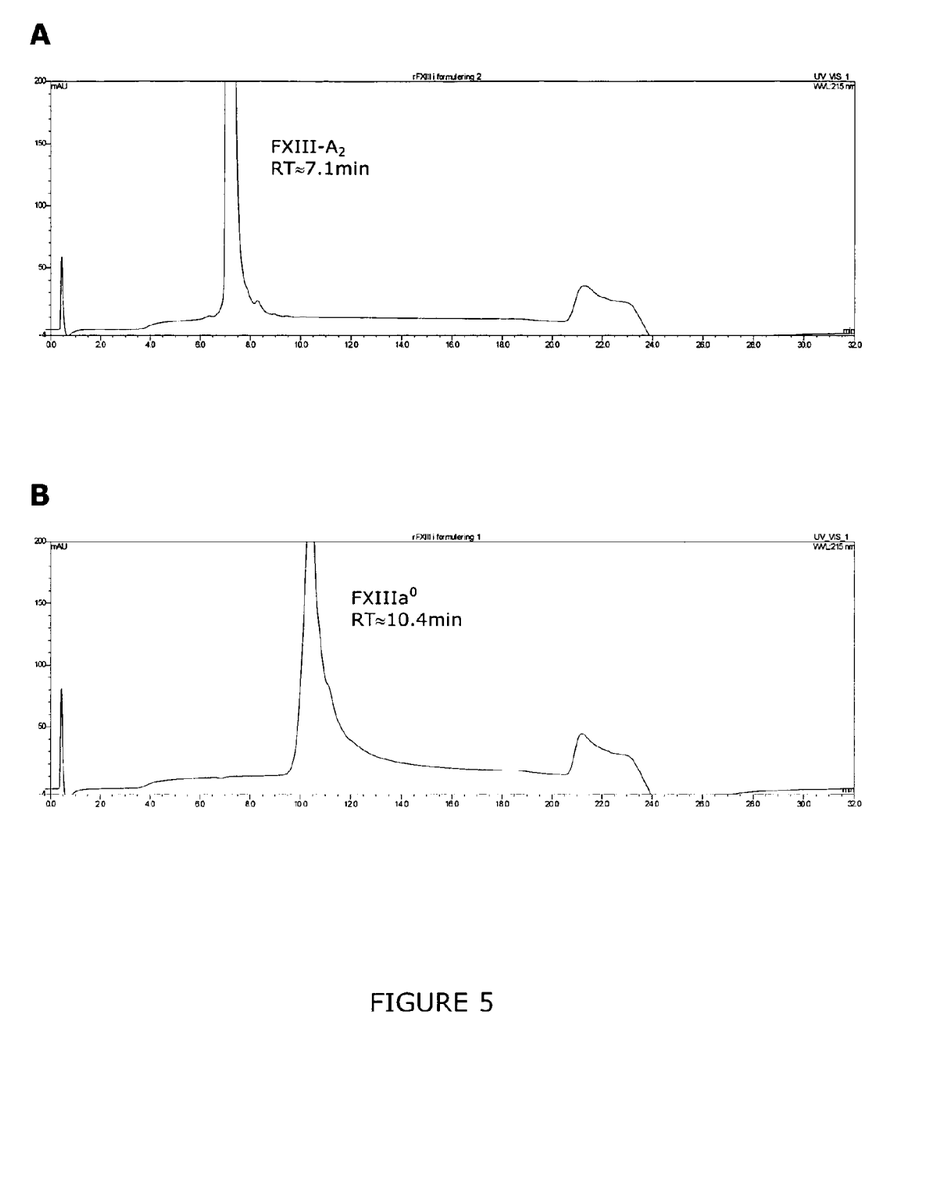

It has been found that zymogen FXIII and FXIIIa$^O$ have different elution profiles and retention times. For example, it can be seen in FIG. 5 that zymogen FXIII has a retention time of 7.1 minutes (FIG. 5A) and FXIIIa$^O$ has a retention time of 10.4 minutes (FIG. 5B). The anion exchange method is able to detect the FXIII and FXIIIa$^O$ as two baseline separated peaks. The eluted fractions obtained from the peak shown in FIG. 5B were collected and tested for FXIIIa$^O$ activity in accordance with the assay described herein and were found to contain 100% FXIIIa$^O$. The limit of FXIIIa$^O$ detection has been advantageously demonstrated to be as little as 0.1-0.2% FXIIIa$^O$ which indicates that the chromatographic separation technique is both a sensitive and rapid quality control method. Furthermore, the chromatographic detection method is also capable of measuring FXIIIa$^O$ without interference from any assay components, thereby eliminating the possibility of in situ activation during analysis.

In one embodiment of the chromatographic separation, the anion exchange HPLC comprises the use of an anion exchange column such as a DEAE-anion or Q-anion column. In a further embodiment, the anion exchange column comprises a DEAE-anion column (e.g. TSKgel DEAE-NPR (Tosoh Bioscience LLC)).

It will be readily apparent to the skilled person that the chromatographic separation step would be carried out in accordance with known procedures, for example the use of equilibrating and elution buffers.

It will be appreciated that the equilibrating and elution buffers will be desirably selected based upon an inability to form insoluble salts, such as calcium. Thus, in one embodiment of the chromatographic separation, the equilibrating and elution buffers comprise Tris at a concentration of between 20 and 100 mM (e.g. 50 mM).

In one embodiment of the chromatographic separation, the equilibrating and elution buffers are buffered to a pH of between 7 and 8 (e.g. 7.5).

In one embodiment of the chromatographic separation, the equilibrating and elution buffers contain at least 2 mM Ca$^{2+}$. In a further embodiment, the equilibrating and elution buffers contain between 3 mM and 5 mM Ca$^{2+}$.

In one embodiment of the chromatographic separation, the elution step is performed by increasing the ionic strength which may be obtained by increasing the concentration of a chosen salt, for example, NaCl between 200 mM and 700 mM (e.g. 500 mM).

In one embodiment, the method additionally comprises the steps of detecting the presence of pre-activated FXIII (FXIIIa$^O$) and measuring the concentration of pre-activated FXIII (FXIIIa$^O$) in said sample.

In one embodiment, the step of measuring the concentration of pre-activated FXIII (FXIIIa$^O$) comprises measuring the activity of FXIII in the presence and absence of thrombin.

According to a further aspect of the invention there is provided a method of measuring the concentration of pre-activated FXIII (FXIIIa$^O$) which comprises measuring the activity of FXIII in the presence and absence of thrombin.

This aspect of the invention allows the percentage of pre-activated FXIII to be calculated as the percentage of total FXIII activity. The total activity measured after addition of thrombin is comprised of the activity generated by activation by thrombin plus the pre-activated already present in the sample (if any). For example:

$$\% \ FXIIIa^O = \frac{\text{pre-activated } FXIII(FXIII \text{ activity in absence of } thrombin)}{\text{activated } FXIII(FXIII \text{ activity in presence of } thrombin)} \times 100$$

In one embodiment, the step of measuring activated/pre-activated FXIII comprises analysis in the presence of a FXIII substrate, i.e. fluorescent or non-fluorescent (i.e. light absorbing) analysis.

In one embodiment, the step of measuring activated/pre-activated FXIII comprises fluorometric analysis in the presence of a fluorescent substrate.

In a further embodiment, the fluorescent substrate is one which may be cleaved by a transglutaminase. In a yet further embodiment, the fluorescent substrate is Abz-NE(Cad-Dnp)EQVSPLTLLK (SEQ ID 1) (ZEDIRA GmbH, Roesslerstrasse 83, D-64293 Darmstadt, Germany—Product Number A101). According to a further aspect of the invention there is provided the use of Abz-NE(Cad-Dnp)EQVSPLTLLK (SEQ ID 1) in the measurement of pre-activated FXIII (FXIIIa$^O$).

Without being bound by theory, it is believed that in the presence of a glycin-ethyl ester, FXIII cleaves a quencher (Cad-Dnp) from the side chain of Abz-NE(Cad-Dnp)EQVSPLTLLK (SEQ ID 1) and incorporates said ester group.

In a further embodiment, activated/pre-activated FXIII is measured in accordance with the methods described in WO 2006/018164 (N-Zyme Biotec GmBH) the measurement methods of which are herein incorporated by reference.

Figure 1:
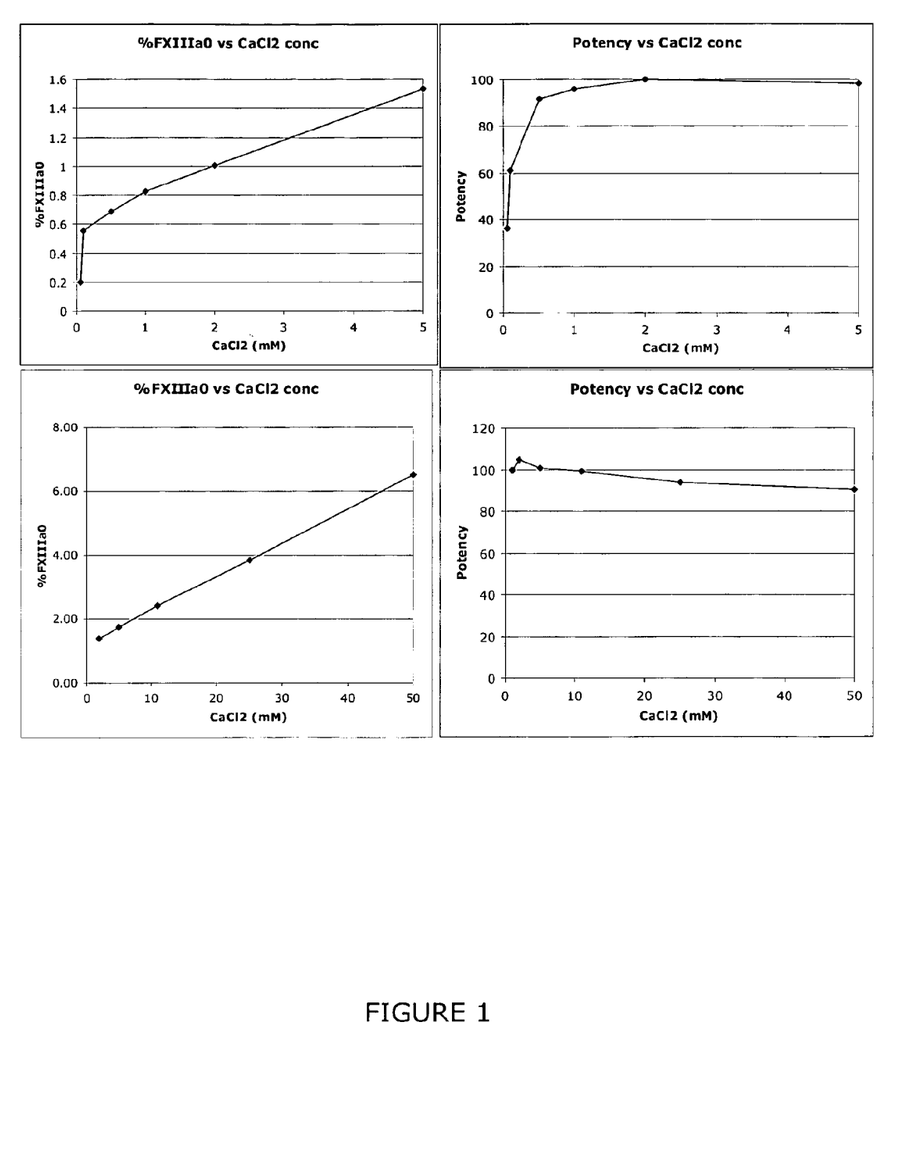
FIG. 1 shows FXIII potency and % FXIIIa$^O$ measured in the presence of varying amounts of Ca$^{2+}$. Left panels show % FXIIIa$^O$, right panels show relative potency. Upper panels show from 0.05 mM to 5 mM Ca$^{2+}$ and lower panels show from 1 mM to 50 mM Ca$^{2+}$.

In one embodiment, activated/pre-activated FXIII is measured in the presence of 0.5-10 mM Ca$^{2+}$. In a further embodiment, activated/pre-activated FXIII is measured in the presence of 1-2 mM Ca$^{2+}$. It has been found to be desirable to maintain the calcium concentration below 2 mM because the determination of % FXIIIa$^O$ is dependent upon calcium concentration (which can be seen from the analysis shown in FIG. 1). In a further embodiment, activated/pre-activated FXIII is measured in the presence of 2 mM Ca$^{2+}$. The benefit of selecting 2 mM Ca$^{2+}$ is that this value is close to the physiological value and therefore best mimics the in vivo situation.

In one embodiment, the Ca$^{2+}$ will be present as atomic absorption standard Ca$^{2+}$ (which may be purchased from Fluka or Sigma-Aldrich). The advantage of using atomic absorption standard $Ca^{2+}$ is that the concentration of $Ca^{2+}$ has been precisely monitored and kept under control under acidic conditions. By contrast, basic conditions undesirably cause the formation of insoluble calcium hydroxide and calcium oxide. Furthermore, atomic absorption standard $Ca^{2+}$ does not suffer from the disadvantages demonstrated by calcium chloride powder. For example, the calcium chloride powder will typically capture moisture from the surroundings and rapidly become inaccurate in the hydration level of the calcium chloride salt, thus precluding accurate weighing of a given molar amount of $Ca^{2+}$.

It will be appreciated that the length of time between incubation of the sample with the assay components and measurement of activated/pre-activated FXIII should be minimised in order to minimise the risk of non-proteolytic activation of FXIII. Thus, in one embodiment the length of time between incubation of the sample with the assay components and measurement of activated/pre-activated FXIII is less than 1 hour.

Figure 2:
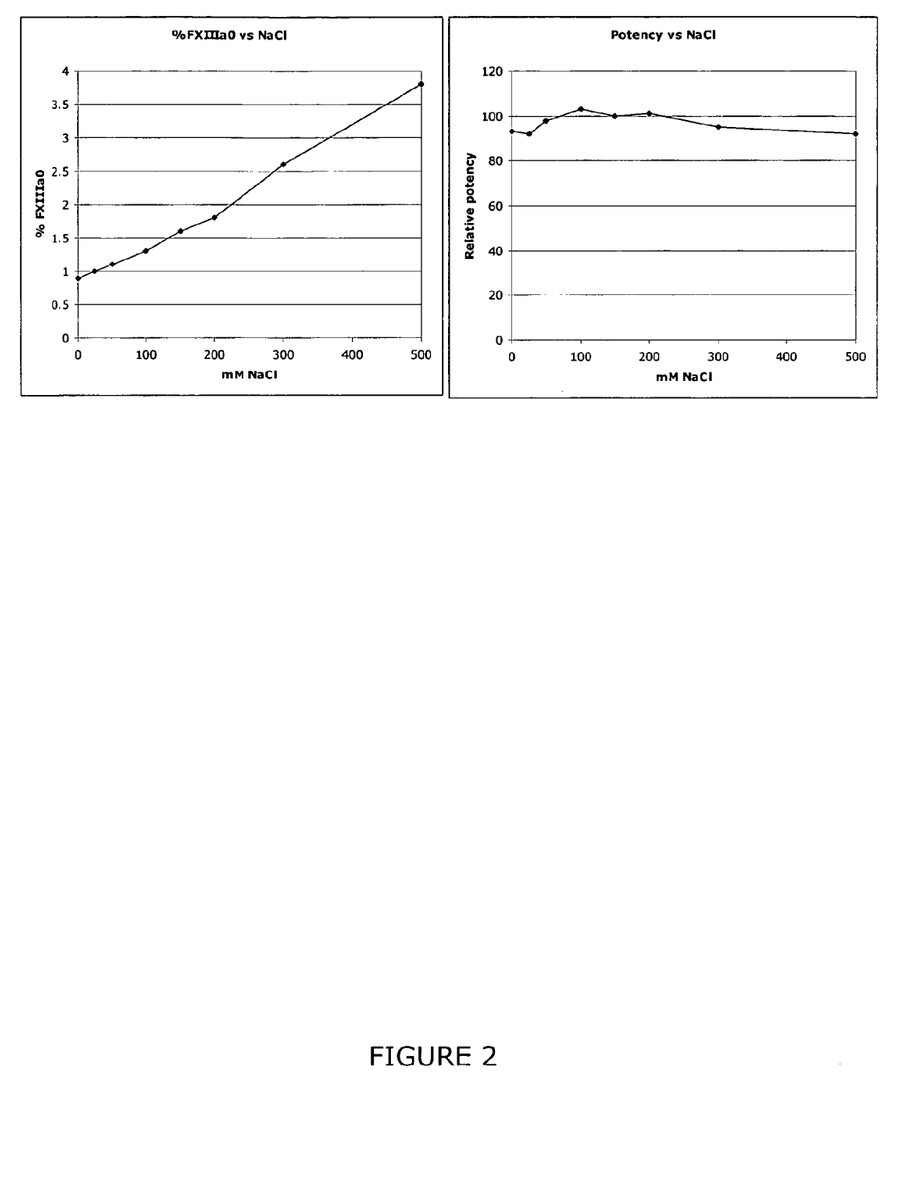
FIG. 2 shows FXIII potency and % FXIIIa$^O$ measured in the presence of varying amounts of NaCl. Left panel shows % FXIIIa$^O$, right panel shows relative potency normalized to 150 mM NaCl.

In one embodiment, activated/pre-activated FXIII is measured in the presence of 50-500 mM NaCl. In a further embodiment, activated/pre-activated FXIII is measured in the presence of 100-200 mM NaCl. It has been found to be desirable to control the concentration of NaCl in the assay because % $FXIIIa^O$ is influenced by a fluctuating NaCl concentration (which can be seen from the analysis shown in FIG. 2). In a yet further embodiment, the concentration of FXIII is measured in the presence of 150 mM NaCl. The benefit of selecting 150 mM NaCl is that this value is close to the physiological value and therefore best mimics the in vivo situation.

Figure 3:
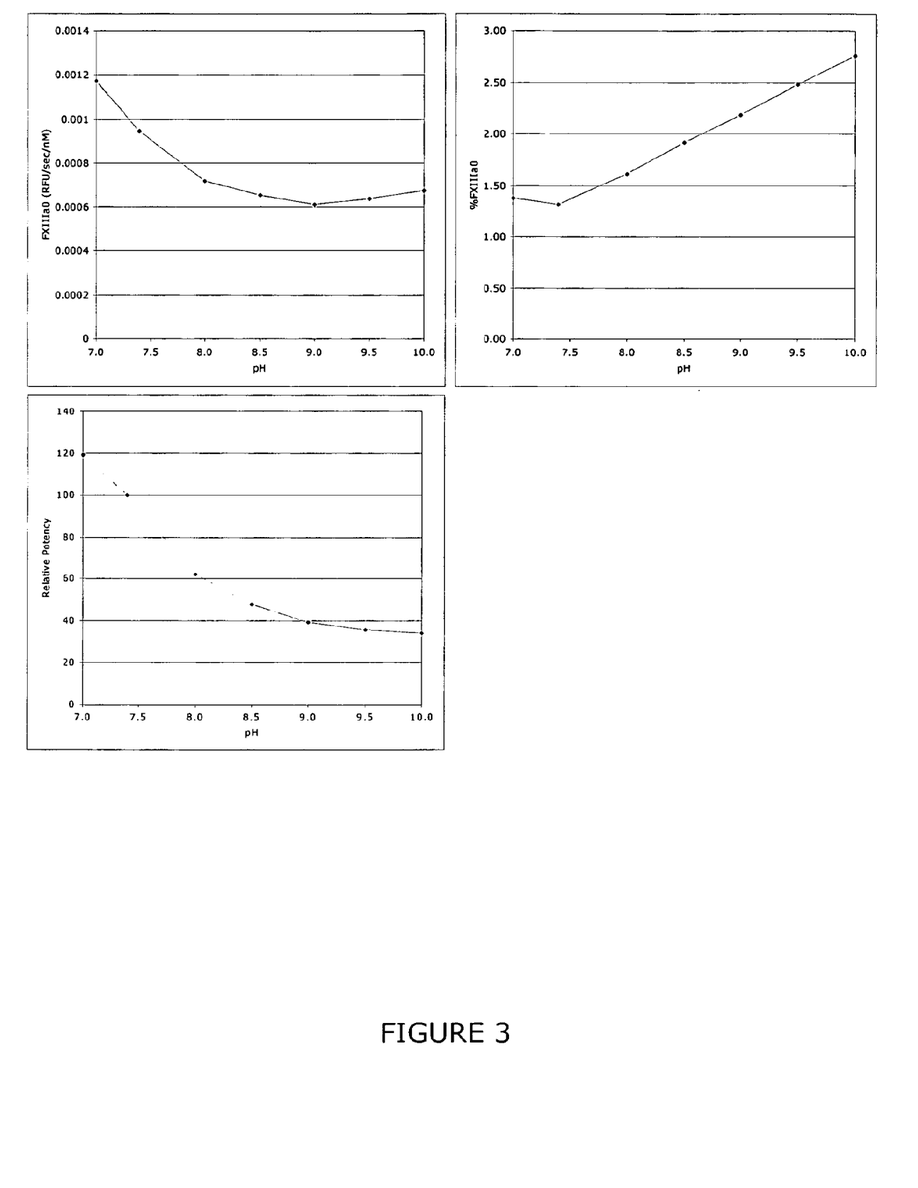
FIG. 3 shows potency, FXIIIa$^O$ and % FXIIIa$^O$ measured as a function of pH. Upper left panel is FXIIIa$^O$ activity in RFU/sec/nM, lower left panel is relative potency as a function of pH and upper right panel is the resulting % FXIIIa$^O$. The relative potency is normalized to pH 7.4.

In one embodiment, activated/pre-activated FXIII is measured at a pH of between 6.5 and 10. In a further embodiment, activated/pre-activated FXIII is measured at a pH of between 7 and 8. It has been found to be desirable to control the pH of the assay because pH has been found to influence both potency and % $FXIIIa^O$ (which can be seen from the analysis shown in FIG. 3). For example, the active site of FXIII* has been found to be influenced by pH. In a yet further embodiment, activated/pre-activated FXIII is measured at a pH of 7.4. The benefit of selecting a pH of 7.4 is that this value is close to the physiological value and therefore best mimics the in vivo situation.

Figure 4:
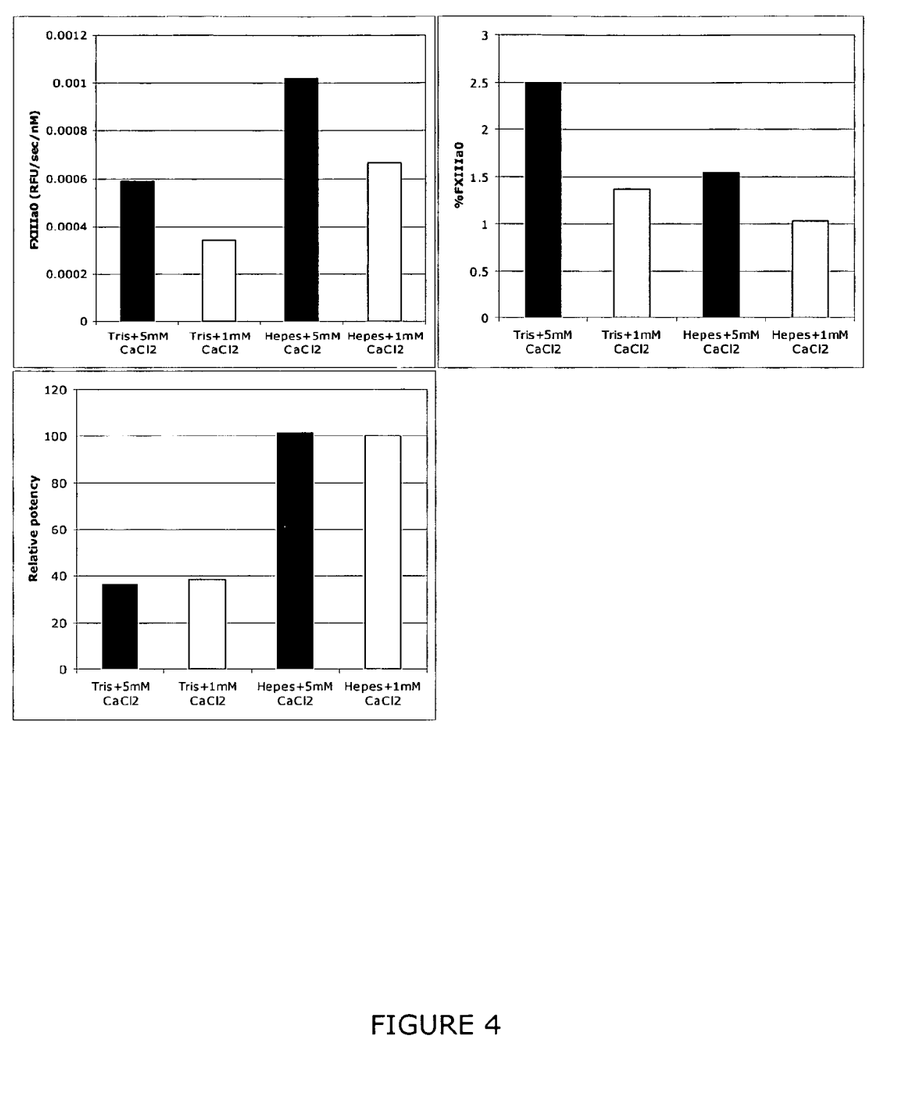
FIG. 4 shows the influence of the buffer component on potency, FXIIIa$^O$ and % FXIIIa$^O$. The upper left panel demonstrates FXIIIa$^O$ activity in RFU/sec/nM, the lower left panel demonstrates relative potency as a function of buffer and Ca$^{2+}$ and the upper right panel demonstrates the resulting % FXIIIa$^O$. All assays were performed at pH 7.4 in the buffer component and 1 or 5 mM Ca$^{2+}$ as indicated. Relative potency was normalized to Hepes with 1 mM CaCl$_2$.

It will be appreciated that activated/pre-activated FXIII will generally be measured in the presence of a buffer capable of buffering to a pH of between 7 and 8 (e.g. 7.4). In one embodiment, activated/pre-activated FXIII is measured in the presence of Hepes buffer. The recommended buffer for Abz-NE(Cad-Dnp)EQVSPLTLLK (SEQ ID 1) is 50 mM Tris adjusted to pH 7.5 using hydrochloric acid. However, it has been found that the choice of buffer has a great impact upon both potency and % $FXIIIa^O$. For example, lower values of % $FXIIIa^O$ were surprisingly measured for Hepes which suggested that Tris may induce new in situ $FXIIIa^O$ (see FIG. 4). This is clearly detrimental during quality testing because a false value may result in unnecessary discarding of batches of FXIII containing formulations. In a further embodiment, activated/pre-activated FXIII is measured in the presence of 50-200 mM Hepes buffer (e.g. 100 mM).

In one embodiment, activated/pre-activated FXIII is measured in the presence of a surfactant. In a further embodiment, the surfactant is a polyethylene glycol surfactant (e.g. PEG 8000). When present, the surfactant will typically be present in an amount of between 0.05 and 0.5% (e.g. 0.1%).

According to a second aspect of the invention there is provided a quality control kit for determining the quality of a Factor XIII (FXIII) containing sample which comprises pre-activated FXIII ($FXIIIa^O$) detecting and/or measuring components and instructions to use said kit in accordance with the methods as defined herein.

In one embodiment, the detecting components comprise an anion exchange HPLC column, such as a DEAE-anion column (e.g. TSKgel DEAE-NPR). In a further embodiment, the detecting components additionally comprise equilibration and elution buffers as hereinbefore defined.

In one embodiment, the measuring components comprise a fluorescent substrate as hereinbefore defined (e.g. Abz-NE(Cad-Dnp)EQVSPLTLLK (SEQ ID 1)). In a further embodiment, the measuring components additionally comprise $Ca^{2+}$ (e.g. 2 mM of atomic absorption standard $Ca^{2+}$). In a yet further embodiment, the measuring components additionally comprise 100-200 mM NaCl (e.g. 150 mM NaCl). In a yet further embodiment, the measuring components additionally comprise 50-200 mM Hepes buffer (e.g. 100 mM) buffered to a pH of between 6.5 and 10 (e.g. 7.4). In a yet further embodiment, the measuring components additionally comprise between 0.05 and 0.5% (e.g. 0.1%) of a surfactant (e.g. PEG 8000).

The invention will now be described with reference to the following non-limited Examples:

Examples

Example 1

HPLC Detection of $FXIIIa^O$

A sample containing FXIII can be subjected to anion exchange HPLC analysis in accordance with the conditions described in Table 1 to detect and quantify the presence of $FXIIIa^O$.

TABLE 1

| | |
|---|---|
| Column: | TSKgel DEAE-NPR 4.6 × 35 mm + guard 4.6 × 5 mm |
| Column temp.: | 25° C. |
| Flow rate: | 1 ml/min |
| Buffer A: | 50 mM Tris, pH 7.5 + 3 mM $CaCl_2$ |
| Buffer B: | 50 mM Tris, pH 7.5 + 500 mM NaCl + 5 mM $CaCl_2$ |
| Gradient: | T = 0, 1% B, T = 2-17.2 min, from 1% B to 27% B, T = 17.2-19.2 min, isocratic at 27% B, T = 19.2-19.7 min, from 27% B to 70% B, T = 19.7-21.7 min from 70% to 90% B and at T = 23.0 min back to 1% B buffer. |
| Autosampler temp.: | Ambient temperature, ~21° C. |
| Injection volume: | ~20 µl or 10-20 µg |
| Detection: | 215 nm |
| Run time: | 32 min |

% $FXIIIa^O$ is determined as the percentage area of the peak representing $FXIIIa^O$ of the total integrated area of the sample. For example, as shown in FIG. 5.

Example 2

Fluorescent Measurement of $FXIIIa^O$ Activity

The activity of FXIII in the presence of thrombin was measured by typically adding a 200 µl reaction mixture containing the components listed in Table 2 to a 96 well microtitre plate.

TABLE 2

| Component | Final assay concentration |
|---|---|
| rFXIII | 0-80 nM |
| Thrombin | 0.24 NIH/mL |
| 2.5M Glycine ethyl ester (amine-donor) | 10 mM |
| Abz-NE(Cad-Dnp)EQVSPLTLLK (substrate) | 30 µM |
| PEG8000 | 0.1% |
| NaCl | 150 mM |
| $Ca^{2+}$ | 2 mM |
| Hepes buffer, pH 7.4 | 100 mM |

Fluorescence was then monitored at an emission of 418 nm and excitation of 313 nm. Typically, the fluorescence was monitored on a plate reader (e.g. SpectraMax Gemini EM from Molecular Devices) using SoftMaxPro software.

The activity of FXIII in the absence of thrombin was measured by typically adding a 200 µl reaction mixture containing the components listed in Table 3 to a 96 well microtitre plate. The measurements of FXIII in the presence or absence of thrombin were ensured to be on the same plate to provide the most accurate comparison of fluorescent signal.

TABLE 3

| Component | Final assay concentration |
|---|---|
| rFXIII | 0-10 000 nM |
| Thrombin | none |
| 2.5M Glycine ethyl ester (amine-donor) | 10 mM |
| Abz-NE(Cad-Dnp)EQVSPLTLLK (substrate) | 30 µM |
| PEG8000 | 0.1% |
| NaCl | 150 mM |
| $Ca^{2+}$ | 2 mM |
| Hepes buffer, pH 7.4 | 100 mM |

Figure 6:
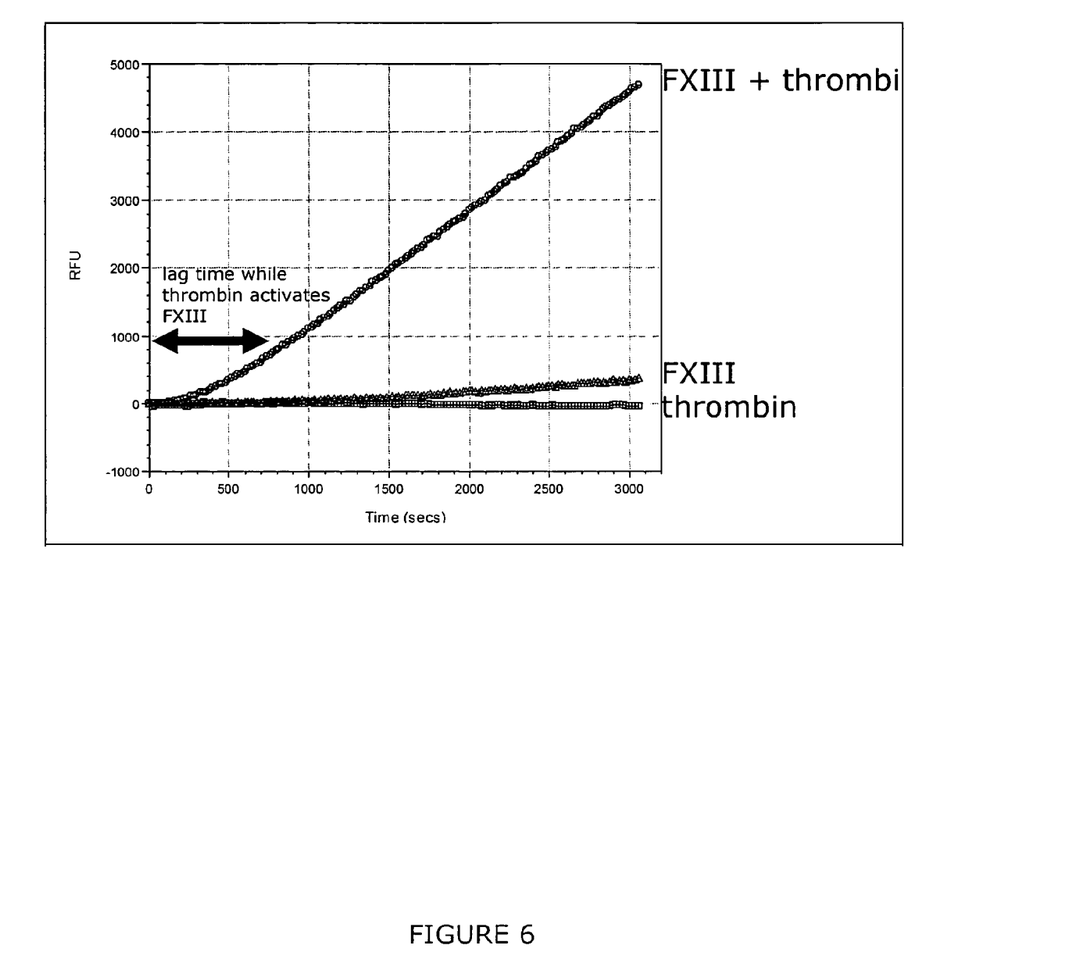
FIG. 6 shows the assay principle showing the signal from FXIII+ thrombin and in the absence of thrombin. In the absence of FXIII no increase in fluorescence over time is detected.

Fluorescence was then monitored in an analogous manner to that described above and the results can be seen in FIG. 6. Activity in the presence and absence of thrombin was then measured in RFU/sec/nM of FXIII (where RFU is relative fluorescent units) and % rFXIIIa$^O$ was calculated as the ratio of the two measurements.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar references in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

Preferred features of the invention:

1. A method of quality control testing a FXIII containing sample which comprises the step of detecting the presence of and/or measuring the concentration of pre-activated FXIII (FXIIIa$^O$) in said sample.

2. A method as defined in clause 1 wherein the presence of FXIIIa$^O$ in said sample is detected by chromatographic separation.

3. A method as defined in clause 2 wherein the chromatographic separation comprises anion exchange HPLC.

4. A method as defined in clause 3 wherein the anion exchange HPLC comprises an anion exchange column such as a DEAE-anion or Q-anion column.

5. A method as defined in clause 4 wherein the anion exchange column comprises a DEAE-anion column such as TSKgel DEAE-NPR.

6. A method as defined in any of clauses 2 to 5 wherein the equilibrating and elution buffers comprise Tris at a concentration of between 20 and 100 mM (e.g. 50 mM).

7. A method as defined in any of clauses 2 to 6 wherein the equilibrating and elution buffers are buffered to a pH of between 7 and 8, such as 7.5.

8. A method as defined in any of clauses 2 to 7 wherein the equilibrating and elution buffers contain at least 2 mM $Ca^{2+}$.

9. A method as defined in clause 8 wherein the equilibrating and elution buffers contain between 3 mM and 5 mM $Ca^{2+}$.

10. A method as defined in any of clauses 2 to 9 wherein the elution buffer additionally comprises between 200 mM and 700 mM NaCl, such as 500 mM.

11. A method as defined in clause 1 which comprises the steps of detecting the presence of pre-activated FXIII (FXIIIa$^O$) and measuring the concentration of pre-activated FXIII (FXIIIa$^O$) in said sample.

12. A method as defined in clause 11 wherein the step of measuring the concentration of pre-activated FXIII (FXIIIa$^O$) comprises measuring the activity of FXIII in the presence (activated FXIII) and absence (pre-activated FXIII) of thrombin.

13. A method as defined in clause 12 wherein the step of measuring activated/pre-activated FXIII comprises fluorometric analysis in the presence of a fluorescent or non-fluorescent FXIII substrate.

14. A method as defined in clause 12 wherein the step of measuring activated/pre-activated FXIII comprises fluorometric analysis in the presence of a fluorescent FXIII substrate.

15. A method as defined in clause 14 wherein the fluorescent substrate is one which may be cleaved by a transglutaminase.

16. A method as defined in clause 15 wherein the fluorescent substrate is Abz-NE(Cad-Dnp)EQVSPLTLLK (SEQ ID 1).

17. A method as defined in any of clauses 12 to 16 wherein activated/pre-activated FXIII is measured in the presence of 0.5-10 mM $Ca^{2+}$, such as 1-2 mM $Ca^{2+}$, 18. A method as defined in clause 17 wherein activated/pre-activated FXIII is measured in the presence of 2 mM $Ca^{2+}$.

19. A method as defined in clause 17 wherein the source of Ca2+, the concentration of Ca2+ has been precisely monitored and kept under control under acidic conditions".

20. A method as defined in clause 17 or clause 18 wherein $Ca^{2+}$ is present as atomic absorption standard $Ca^{2+}$.

21. A method as defined in any of clauses 12 to 20 wherein activated/pre-activated FXIII is measured in the presence of 50-500 mM NaCl, such as 100-200 mM NaCl.
22. A method as defined in clause 21 wherein activated/pre-activated FXIII is measured in the presence of 150 mM NaCl.
23. A method as defined in any of clauses 12 to 22 wherein activated/pre-activated FXIII is measured at a pH of between 6.5 and 10, such as between 7 and 8.
24. A method as defined in clause 23 wherein activated/pre-activated FXIII is measured at a pH of 7.4.
25. A method as defined in any of clauses 12 to 24 wherein activated/pre-activated FXIII is measured in the presence of Hepes buffer.
26. A method as defined in clause 25 wherein activated/pre-activated FXIII is measured in the presence of 50-200 mM Hepes buffer, such as 100 mM.
27. A method as defined in any of clauses 12 to 26 wherein the concentration of FXIII is measured in the presence of a surfactant.
28. A method as defined in clause 27 wherein the surfactant is a polyethylene glycol surfactant, such as PEG 8000.
29. A method as defined in clause 27 or clause 28 wherein the surfactant is present in an amount of between 0.05 and 0.5%, such as 0.1%.
30. A quality control kit for determining the quality of a Factor XIII (FXIII) containing sample which comprises pre-activated FXIII (FXIIIa$^O$) detecting and/or measuring components and instructions to use said kit in accordance with the methods as defined in any preceding clauses.
31. A kit as defined in clause 30 wherein the detecting components comprise an anion exchange HPLC column as defined in clause 4 or clause 5.
32. A kit as defined in clause 30 or clause 31 wherein the detecting components additionally comprise equilibration and elution buffers as defined in any of clauses 6 to 10.
33. A kit as defined in clause 30 wherein the measuring components comprise a fluorescent substrate as defined in clause 15 or clause 16.
34. A kit as defined in clause 33 wherein the measuring components additionally comprise $Ca^{2+}$, such as 2 mM of atomic absorption standard $Ca^{2+}$.
35. A kit as defined in clause 33 or clause 34 wherein the measuring components additionally comprise 100-200 mM NaCl, such as 150 mM NaCl.
36. A kit as defined in any of clauses 33 to 35 wherein the measuring components additionally comprise 50-200 mM Hepes buffer, such as 100 mM Hepes buffer.
37. A kit as defined in clause 36 wherein the Hepes buffer is buffered to a pH of between 7 and 8, such as 7.4.
38. A kit as defined in any of clauses 33 to 37 wherein the measuring components additionally comprise between 0.05 and 0.5% of a surfactant, such as 0.1% PEG 8000.
39. Use of Abz-NE(Cad-Dnp)EQVSPLTLLK (SEQ ID 1) in the measurement of pre-activated FXIII (FXIIIa$^O$).
40. A method of detecting the presence of and/or measuring the concentration of pre-activated FXIII (FXIIIa$^O$) which comprises a chromatographic separation step.
41. A method of measuring the concentration of pre-activated FXIII) (FXIIIa$^O$ which comprises measuring the activity of FXIII in the presence and absence of thrombin.

The invention claimed is:
1. A method of quality control testing a sample containing Factor XIII (FXIII) by determining the level of pre-activated FXIII in the sample, comprising:
measuring activated FXIII in the sample in the absence of thrombin and in the presence of 0.5-10 mM atomic absorption standard $Ca^{2+}$; and
measuring activated FXIII in the sample in the presence of thrombin and 0.5-10 mM atomic absorption standard $Ca^{2+}$,
wherein the ratio of (i) activated FXIII in the absence of thrombin to (ii) activated FXIII in the presence of thrombin indicates the level of pre-activated FXIII in the sample.
2. The method according to claim 1, wherein the measuring steps comprise measuring the activated FXIII in the presence of 1-2 mM atomic absorption standard $Ca^{2+}$.
3. The method according to claim 2, wherein the measuring steps comprise measuring the activated FXIII in the presence of 2 mM atomic absorption standard $Ca^{2+}$.
4. The method according to claim 1, wherein the measuring steps are performed in the presence of a fluorometric or non-fluorometric substrate.
5. The method according to claim 4, wherein the substrate comprises Abz-NE(Cad-Dnp)EQVSPLTLLK.
6. The method according to claim 1, wherein the measuring steps further comprise measuring the activated FXIII in the presence of 50-500 mM NaCl.
7. The method according to claim 6, wherein the measuring steps further comprise measuring the activated FXIII in the presence of 100-200 mM NaCl.
8. The method according to claim 1, wherein the measuring steps further comprise measuring the activated FXIII at a pH between 6.5 and 10.
9. The method according to claim 8, wherein the measuring steps further comprise measuring the activated FXIII at a pH between 7 and 8.
10. The method according to claim 1, wherein the measuring steps further comprise measuring the activated FXIII in the presence of 50-200 mM Hepes buffer.

11. The method according to claim 10, wherein the measuring steps further comprise measuring the activated FXIII in the presence of 100 mM Hepes buffer.

12. The method according to claim 1, wherein the measuring steps further comprise measuring the activated FXIII in the presence of a surfactant.

13. The method according to claim 12, wherein the surfactant is a polyethylene glycol.

* * * * *